United States Patent [19]

Lamb et al.

[11] E Patent Number: Re. 33,621

[45] Reissued Date of Patent: Jun. 25, 1991

[54] ANATOMIC BRACE FRACTURE FOR THE KNEE

[76] Inventors: Steve R. Lamb, 6724 Corte Del Vista, Pleasanton, Calif. 94566; Robert R. Moore, 1897 National Ave., Hayward, Calif. 94577

[21] Appl. No.: 246,260

[22] Filed: Sep. 19, 1988

Related U.S. Patent Documents

Reissue of:

[64] Patent No.: 4,523,585
Issued: Jun. 18, 1985
Appl. No.: 538,120
Filed: Oct. 3, 1983

U.S. Applications:

[63] Continuation of Ser. No. 828,453, Feb. 11, 1986, abandoned, which is a continuation-in-part of Ser. No. 315,424, Oct. 27, 1981, abandoned.

[51] Int. Cl.[5] ..... A61F 5/04; A61F 3/00
[52] U.S. Cl. ..... 128/80 C; 623/39
[58] Field of Search ..... 128/80 C, 80 F; 623/39

[56] References Cited

U.S. PATENT DOCUMENTS

| | | | |
|---|---|---|---|
| 2,208,275 | 7/1940 | McCann | 3/22 |
| 2,638,605 | 5/1953 | Johnson | 3/22 |
| 2,877,033 | 3/1959 | Koetke | 128/80 F |
| 3,785,372 | 1/1974 | Craig | 120/80 C |
| 3,823,424 | 7/1974 | May | 3/22 |
| 3,826,251 | 7/1974 | Ross | 128/80 F |
| 3,827,431 | 8/1974 | Pecorella | 128/80 F |
| 3,885,252 | 5/1975 | Nakajima | 128/80 C |
| 3,901,223 | 8/1975 | May | 120/80 F |
| 3,902,482 | 9/1975 | Taylor | 128/80 F |
| 4,136,404 | 1/1979 | Lange | 128/80 R |
| 4,145,766 | 3/1979 | May | 3/22 |
| 4,245,629 | 1/1981 | Cummins | 128/80 C |
| 4,256,097 | 3/1981 | Willis | 120/80 C |
| 4,268,923 | 5/1981 | Stofferi | 3/22 |
| 4,323,059 | 4/1982 | Rombert et al. | 120/80 C |
| 4,337,764 | 7/1982 | Lerman | 128/80 F |
| 4,340,041 | 7/1982 | Frank | 128/88 |
| 4,361,142 | 11/1982 | Lewis | 128/80 C |
| 4,372,298 | 2/1983 | Lerman | 128/80 C |
| 4,379,463 | 4/1983 | Meier et al. | 128/80 C |
| 4,407,276 | 10/1983 | Bledsoe | 128/80 C |
| 4,463,751 | 8/1984 | Bledsoe | 128/80 C |
| 4,493,316 | 1/1985 | Reed et al. | 128/80 C |
| 4,506,661 | 3/1985 | Foster | 128/80 C |
| 4,524,764 | 6/1985 | Miller et al. | 128/80 C |
| 4,554,913 | 11/1985 | Womack | 128/80 C |

FOREIGN PATENT DOCUMENTS

| | | | |
|---|---|---|---|
| 841190 | 4/1952 | Fed. Rep. of Germany . | |
| 1491569 | 7/1969 | Fed. Rep. of Germany | 128/80 F |
| 736141 | 11/1932 | France . | |
| 982500 | 6/1951 | France . | |

OTHER PUBLICATIONS

"Kinematics of the Human Knee Joint", IBM New York Scientific Center Report No. 320-2928, Jan. 1968.

*Primary Examiner*—Edgar S. Burr
*Assistant Examiner*—Tonya Lamb
*Attorney, Agent, or Firm*—Bielen & Peterson

[57] ABSTRACT

An anatomic fracture brace mechanism for knee braces to provide lateral restraint and delimited supportive motion of the knee joint permitting weight bearing ambulation of the patient during healing of leg fractures or other traumas, a fracture brace being constructed with a brace mechanism utilizing an asymmetrical four-bar, cross-linkage to follow, as closely as mechanically practical, the polycentric motion of the human knee.

10 Claims, 2 Drawing Sheets

ANATOMIC BRACE FRACTURE FOR THE KNEE

Matter enclosed in heavy brackets [ ] appears in the original patent but forms no part of this reissue specification; matter printed in italics indicates the additions made by reissue.

*This application is a continuation of our copending reissue application Ser. No. 828,453 filed Feb. 11, 1986, abandoned, which is a reissue application of U.S. Pat. No. 4,523,585, that issued on June 18, 1985 from application Ser. No. 538,120, filed Oct. 3, 1983 which is a contuation-in-part application of application Ser. No. 315,424 filed Oct. 27, 1981, entitled ANATOMIC FRACTURE BRACE FOR THE KNEE and now abandoned.*

BACKGROUND OF THE INVENTION

This invention relates to a knee brace and particularly to a knee brace applied to a patient's knee subsequent a fracture of tibia or femur, or after operation on the knee or in other cases where knee flexion and extension is desired under a restricted and/or supported condition.

It has been found that the traditional immobilization of joints above and below a fractured bone results in undesirable consequences to the joints. While temporary stiffness of the immobilized joint and atrophy of the limb musculature are recognized as an inevitable consequence of such practice, often iatrogenic stiffness and swelling can constitute a severe complication and should be avoided if possible.

It has been discovered that the use of a brace at the site of the knee to allow a degree of motion to the knee joint while providing a connective support between the tibia and femur will substantially reduce the expected joint stiffness and muscle atrophy and will curtail pain and swelling that often accompanied removal of conventional casts which immobilized joints.

Because the knee is not a single-axis joint, the use of a bracing system with a single pivot axis caused pistoning of the leg and either failed to provide the support necessary or caused additional trauma prolonging recovery. Bracing devices employing more than one axis were developed in an attempt to follow the polycentric movement of the knee joint. Most prior art devices employ members with a gear tooth interconnection where two elongated elements each have a gear tooth end and proximately spaced pivotal axis pins interconnected by a connecting link. However, either because the true motion of the knee joint was not correctly understood or for reasons of simplicity, the devices devised did not follow the kinematic motion of the knee and the resultant motion for each element was essentially symmetrical or mirror-like in effect.

One prior art device employed a four-bar link concept which, however, was arranged in a symmetrical manner and essentially duplicated, with some enlargement, the mirror-like motion path common to the gear-type mechanisms.

In the authoritative publication, "Kinematics of the Human Knee Joint", IBM New York Scientific Center Report No. 320-2928, January 1968, the precise motion of the polycentric knee joint was described and defined. Computer aided synthesis was employed by Applicant to duplicate this motion in a mechanism. While exact duplication required mechanics of awkward design, the motion could be closely followed within practical limits by a four-bar linkage with assymetrical positioning of its linkage axes. The resultant motion did not have the mirror-image effect of prior art systems, but parodied the assymetrical motion of the human knee.

SUMMARY OF THE INVENTION

This invention is directed in particular to a four-bar linkage mechanism to achieve a polycentric motion that follows the actual motion of the human knee. The four-bar linkage mechanism is incorporatable into a bracing system for lateral restraint and vertical support of an injured or post operative leg, relieving the knee of aggravating stresses while permitting mobility to the knee and early ambulation of the patient. The linkage mechanism is designed for use in pairs, placed on each side of the patient's knee and located by a marking on the mechanism to specified points on each side of the patient's knee. The pair of linkage mechanisms are fixed in place by conventional means depending on the nature of the knee treatment. For example, in fractures of the tibia or femur, extension members of the linkage mechanisms are incorporated into the leg cast, which is modified to permit motion to the knee joint.

For less traumatic injuries or post-operative or phased treatments, the linkage mechanisms may be strapped or bound to the leg above and below the knee to provide the degree of support and restriction desired.

As noted, the linkage mechanism both restricts lateral displacements of the knee joint and permits a natural supportive motion to the knee. Compressive forces of the femoral condyle on the tibial plateau are relieved during ambulatory motion of the patient. Stiffness and muscle atrophy are prevented and the patient is able to assume a minimally restrictive ambulatory movement substantially earlier than previously allowed. The close conformity of the linkage motion to the actual motion of the knee prevents pistoning of the leg, particularly when cast, preventing undesirable dynamically applied stresses common to prior art systems.

These and other features will become apparent from a detailed description of the preferred embodiments.

DETAILED DESCRIPTION OF THE PREFERRED EMBODIMENTS

Figure 1:
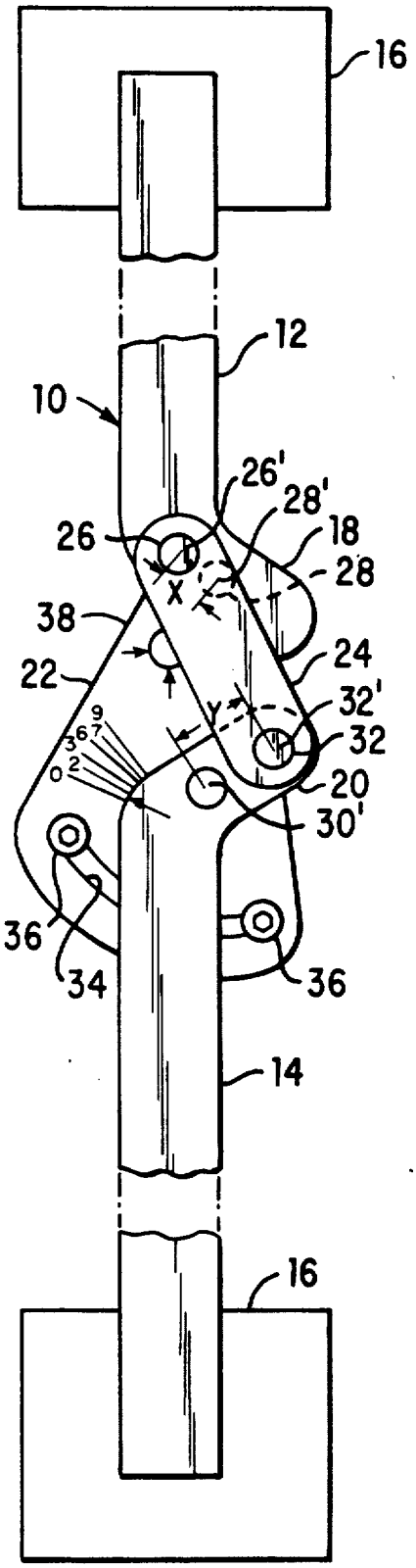
FIG. 1 is a side elevational view of the preferred embodiment of the knee brace mechanism.
Figure 2:
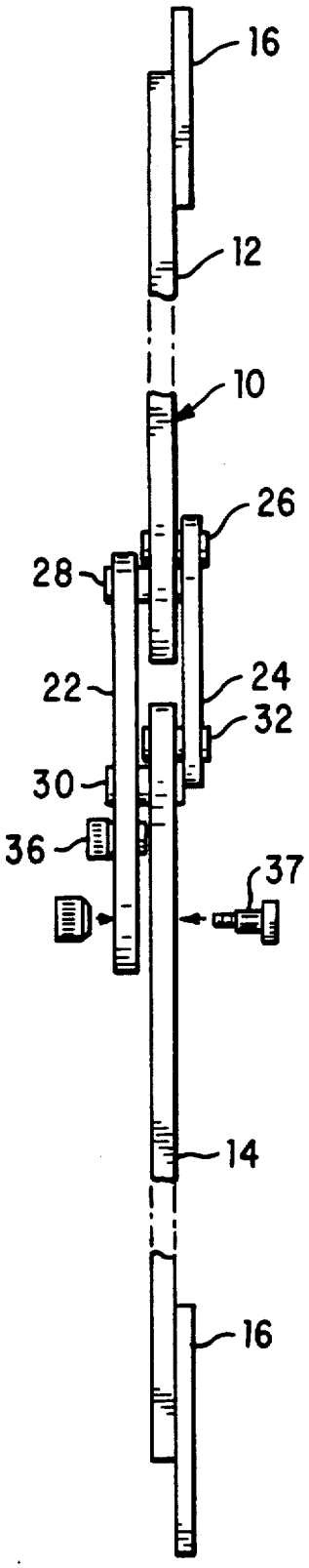
FIG. 2 is an end elevational view of the mechanism of FIG. 1.

Referring to FIGS. 1 and 2, the preferred brace mechanism designated by the reference numeral 10 is shown. The brace mechanism comprises a four-bar linkage system with its links specifically arranged to approximate the polycentric joint movement of the human knee. The brace mechanism 10 has two primary links, an upper extension link 12 which is constructed to extend up the patient's leg for anchoring and a lower extension link 14 which is directed down the patient's leg for anchoring. The precise length of the extensions is not critical and terminal pads 16 may be eliminated depending on the anchoring means employed. In most cases, the extension links will be anchored by incorporation into a leg cast, which after curing is cut at the knee joint to allow pivot at the knee.

The upper and lower extension links are crooked at their connective ends 18,20 to improve alignment of the motion centers of the brace mechanism with the corresponding motions of the knee while maintaining the natural placement and narrow width to the elongated extension links. The crooked ends are spaced from one another and interconnected by crossed connecting links 22 and 24. The crossed connecting links each have two spaced pivotal axes, 26' and 28', and 30' and 32', with interconnecting pivot pins 26, 28, 30 and 32, one connected to the upper extension link 12 and one connected to the lower extension link 14. Each extension link has two axes of connection, one for each connecting link. While the distance between pivotal axes on the two crossed connecting links are substantially equal, the distance "x" between the pivotal axes 26' and 28' on the upper extension link 12 is less than the distance "y" between the pivotal axes 30' and 32' on the lower extension link 14. This symmetrical arrangement of the pivot axes effects the peculiar motion desired. While the distance "x" is approximately ⅜ inch and the distance "y" is approximately ⅝ inch, the specific distance of each is variable allowing adaptations of the mechanisms to small or large bone structure or slight variations in motion, so long as the dimension between the axes on the upper extension link is less than the dimension between the axes on the lower extension link. When the extension links are aligned, the pivots are offset in approximately a [30°] *45°* line from the vertical to optimize the angular displacement of the extension links on bending of the knee.

In the preferred embodiment, the connecting link 22 is plate-like in configuration to accommodate a variable stop to limit articulation of the brace mechanism. Included in the link is a guide slot 34 with slide stops 36 with a flat key face 37 which allows the stop to slide along the slot to restrict articulation at points desired by the attending physican, for example, when only a slight pivot to the knee can be permitted for a serious injury. The relatively large radius of the arc of the slot is designed to reduce stresses on the stops during use.

The degree of articulation permitted by the stops can be adjusted with the aid of an arrow marking 33 stamped on the elbow of the lower extension link 14 in conjunction with scale markings 35 stamped on the plate like connecting link 22. The scale markings indicate the degree of articulation from a vertical alignment of the upper extension link and the lower extension link.

Also located on link 22 are locating marking 39 comprising stamped arrows with a locating hole 38. The hole is used to position and align the extension links of a pair of the brace mechanisms alongside each side of the leg on the TKA (Trochanter, Knee, Ankle) axis with the hole positioned on the bone prominance of the femur which is located and premarked by the physician. The proximate placement of the outer brace mechanism of the pair on a patient is shown in FIG. 5.

Figure 3:
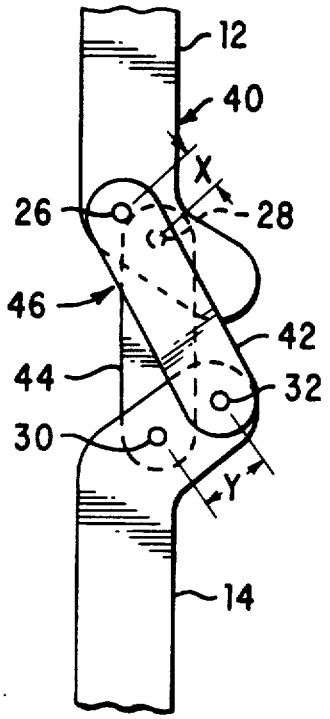
FIG. 3 is a side elevational view of an alternate embodiment of the knee brace mechanism.

Referring to FIG. 3, an alternate embodiment 40 of the brace mechanism is shown. The parts are substantially identical to the mechanism 10 of FIG. 1 and FIG. 2 with the two connecting links 42 and 44 identical in configuration. In this embodiment, no provision is made for a stop mechanism and the alignment means 46 comprises the intersecting point 46 of the back edges of the two connecting cross links when the extension links are aligned. Operationally, the movement is the same.

Figure 4:
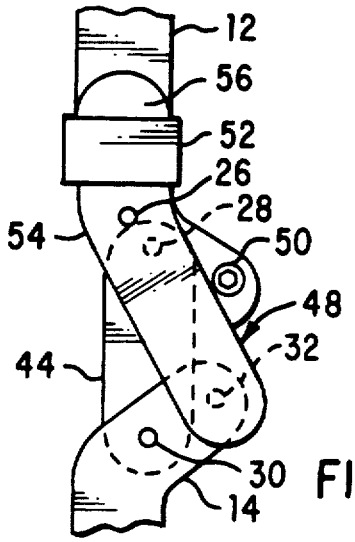
FIG. 4 is a side elevational view of an additional alternate embodiment of the knee brace mechanism.

Referring to FIG. 4 a second alternate embodiment 48 of the brace mechanism is shown. The construction is similar to the embodiment 40 with the addition of a stop pin 50 to limit articulation to a vertical aligned position and a slide lock 52 to lock the brace mechanism in the aligned position. The stop pin 50 is threaded to the toe of the upper extension link 12 and projects therefrom to contact the edge of the modified connecting link 54. The connecting link 54 is modified to include a tab extension 56 which aligns with the upper extension link 12, when the two extension links are aligned. The slide lock 52 comprises a rectangular collar member which slides on the upper extension link 12 and can be lowered to encompass the tab extension 56. This embodiment is used when articulation of the leg at the knee is to be prevented and permitted only during brief periods of supervised exercise or manipulation.

Figure 5:
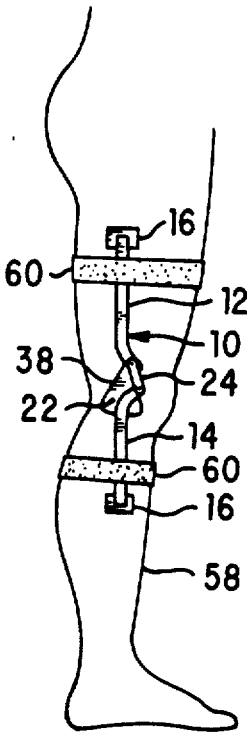
FIG. 5 is a schematic illustration of a brace mechanism located on a user's leg.

Referring to FIG. 5 the brace mechanism 10 is schematically shown on one side of a user's leg 50. It is to be understood that the brace mechanism is used in pairs on either side of the leg for operational support. While a simple tape wrap 60 is shown retaining the mechanism against the leg, in most cases the mechanism would be largely covered by a leg [cost] *cast* or orthopedic bracing, exposing only the linkage portion of the mechanism to permit the desired articulation.

Figure 6:
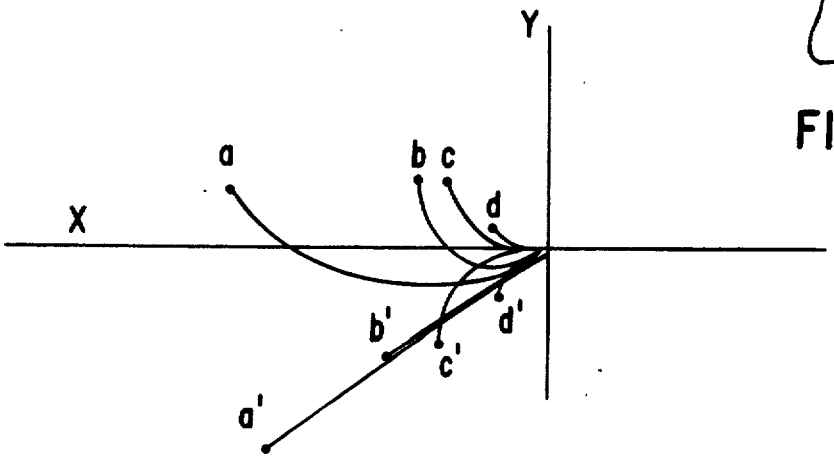
FIG. 6 is a diagrammatic illustration of the motion path of the subject knee brace mechanism in comparison with the actual motion of the knee and other prior art devices.

In FIG. 6 the comparative instant centers of rotation of the human knee a-a', the invented asymmetrical four-bar link mechanism b-b', a prior art symmetrical four-bar link mechanism c-c', and a typical gear-type mechanism d-d' are shown. Progressing from a common [center] *centrodes*, each of the dual [center] *centrodes* diverge as the systems move from alignment (where the leg is straight) to an angled position (where the leg is bent). The non-mirror-like motion of the polycentric human knee and subject brace mechanism with their one curved and one straight trajectories are shown to differ substantially from the mirror-like motions of the prior art systems.

The conformity of motion of the brace mechanism to the actual motion of the knee is important not only for uniformity in the degree of support, but when the extension links are anchored within a cast, to prevent the links from pushing or pulling on the cast in position fashion, which will cause inherent stress on the site of injury.

While in the foregoing embodiments of the invention have been set forth in considerable detail for the purposes of making a complete disclosure of the invention, it should be apparent to those of skill in the art that numerous changes may be made in such details without departing from the spirit and principles of the invention.

What is claimed is:

[1. A brace mechanism having a four-bar linkage for use in a paired arrangement on each side of a user's leg in an anatomic knee brace comprising:

a. a first extension link with an upward extension portion adapted and constructed to align with a user's leg on above the knee, and with a lower portion, having first and second spaced pivots;

b. a second extension link with a downward extension portion adapted and constructed to align with a user's leg below the knee and with an upper end portion having spaced third and fourth pivots, said distance between said third and fourth pivots being greater than said first and second pivots;

c. a third connecting link having a first end connected to said first pivot on said first link and a second end connected to said fourth pivot on said second link;

d. a fourth connecting link having a first end connected to said second pivot or said first link and a second end connected to said third pivot on said second link, said fourth link crossing said third link; wherein upon vertical alignment of said extension portions, said first pivot is located on said end portion of said first link proximate said extension portion and said second pivot is displaced from said first pivot in a downward angled direction and, said third pivot is located on said end portion of said second link proximate said extension portion and said fourth pivot is displaced from said third pivot in an upward angled direction toward said second pivot, whereby said four-bar linkage is constructed and arranged to generate a polycentric motion with dual centers progressing from a common center point when said extension portions are aligned against a user's straight leg and diverging with asymmetric trajectories when said extensions portions are angled conforming to a user's bent leg, the asymmetric trajectories of the four-bar linkage approximately the asymmetric trajectories of the polycentric motion of user's knee.]

[2. The brace mechanism of claim 1 wherein said third and fourth links have an effective length approximately the same.]

[3. The brace mechanism of claim 1 wherein said extension portions on each of said first and second links have a longitudinal axis and said pivots on said end portions 30° from said longitudinal axis of said extension portions.]

[4. The brace mechanism of claim 1 having locating means thereon for locating said brace mechanism alongside a user's knee, said locating means being positioned at the bone pominance of user's fermur at side of the user's knee.]

[5. The brace mechanism of claim 4, wherein said fourth link comprises a flat plate and said locating means comprises a hole in said plate.]

[6. The brace mechanism of claim 1 having adjustable stop means for selectively limiting articulation of said extension portion of said first upper extension link relative to said extension portion of said second lower extension link in said brace mechanism.]

[7. The brace mechanism of claim 6 wherein said stop means comprises first and second moveable stops on said fourth link arranged on each side of said second link.]

[8. The brace mechanism of claim 1 comprising further locking means for locking said brace mechanism with said brace mechanism with said vertical extensions vertically aligned.]

[9. The brace mechanism of claim 8 wherein said third connecting link includes a tab extension which aligns with said extension portion of said first extension link on vertical alignment of said two extension links, said locking means comprising a slide collar slidable on said extension portion of said first extension link and engageable around said tab extension to lock said tab extension to said first extension link thereby locking said brace mechanism.]

[10. The brace mechanism of claim 3 having further stop means for limiting the articulation of said brace mechanism in one direction to vertical alignment of said two extension members.]

*11. A brace mechanism having a four-bar linkage for use in a paired arrangement on each side of a user's leg in an anatomic knee brace comprising:*

*a. a first extension link with an upward extension portion adapted and constructed to align with a user's leg above the knee, and with a lower end portion, having first and second spaced pivots;*

*b. a second extension link with a downward extension portion adapted and constructed to align with a user's leg below the knee, and with an upper end portion having spaced third and fourth pivots, said distance between said third and fourth pivots being greater than said first and second pivots;*

*c. a third connecting link having a first end connected to said first pivot on said first link and a second end connected to said fourth pivot on said second link;*

*d. a fourth connecting link having a first end connected to said second pivot on said first link and a second end connected to said third pivot on said link wherein upon alignment of said extension portions, said first pivot is located on said end portion of said first link proximate said extension portion and said second pivot is spaced from said first pivot in a downward angled direction, said third pivot is located on said end portion of said second link proximate said extension portion and said fourth pivot is spaced from said third pivot in an upward angled direction toward said second pivot; and said fourth link crosses said third link;*

*e. a locating means for aligning the brace mechanism in a paired arrangement on each side of a user's leg, the locating means being positioned at the bone prominence of a user's femur at the side of a user's knee when the brace mechanism is installed on a user; and*

*f. a locking means for locking said brace mechanism with said extension links aligned, wherein said third connecting link includes a tab extension which aligns with said extension portion of said first extension link on alignment of said two extension links, said locking means comprising a slide collar slidable on said extension portion of said first extension link and engageable around said tab extension to lock said tab extension to said first extension link thereby locking said brace mechanism; whereby said four-bar linkage is constructed and arranged to generate a polycentric motion with dual centrodes progressing from a common centrode point when said extension portions are aligned against a user's straight leg and diverging with asymmetric trajectories when said extension portions are angled conforming to a user's bent leg, the asymmetric trajectories of a four-bar linkage approximating the asymmetric trajectories of the polycentric motion of a user's knee.*

*12. A brace mechanism having a four-bar linkage for use in a paired arrangement on each side of a user's leg in an anatomic knee brace comprising:*

*a. a first extension link with an upward extension portion adapted and constructed to align with a user's leg above the knee, and with a lower end portion, having first and second spaced pivots;*

*b. a second extension link with a downward extension portion adapted and constructed to align with a user's leg below the knee and with an upper end portion having spaced third and fourth pivots, said distance between said third and fourth pivots being greater than said first and second pivots;* c. *a third connecting link having a first end connected to said first pivot on said first link and a second end connected to said fourth pivot on said second link;* d. *a fourth connecting link having a first end connected to said second pivot on said first link and a second end connected to said third pivot on said second link wherein upon alignment of said extension portions, said first pivot is located on said end portion of said first link proximate said extension portion and said second pivot is spaced from said first pivot in a downward angled direction, said third pivot is located on said end portion of said second link proximate said extension portion and said fourth pivot is spaced from said third pivot in an upward angled direction toward said second pivot, and said fourth link crosses said third link and,* e. *a locating means on the four bar linkage for aligning the brace mechanism in a paired arrangement on each side of a user's leg in a position which maximizes conformity of the motion of the brace mechanism with the motion of the user's leg, the locating means on one brace mechanism being positionable at the bone prominence of a user's femur at the side of a user's knee when the brace mechanism is installed on a user; wherein said four-bar linkage is constructed and arranged to generate a polycentric motion with dual centrodes progressing from a common centrode point when said extension portions are aligned against a user's straight leg and diverging with asymmetric trajectories when said extension portions are angled conforming to a user's bent leg, the asymmetric trajectories of the four-bar linkage approximating the asymmetric trajectories of the polycentric motion of a user's knee when the locating means is properly positioned at the femur bone prominence and the brace mechanism is properly aligned on each side of the user's leg in said paired arrangement.*

*13. The brace mechanism of claim 12 wherein said third and fourth links have an effective length between pivots which is approximately equal.*

*14. The brace mechanism of claim 12 wherein said extension portions on each of said first and second links have a longitudinal axis and each of said pairs of pivots on said end portions define an axis having an orientation approximately 45° from said longitudinal axis of said extension portions.*

*15. The brace mechanism of claim 12 wherein said fourth link comprises a flat plate and said locating means comprises a hole in said plate.*

*16. The brace mechanism of claim 12 having adjustable stop means for selectively limiting articulation of said extension portion of said first upper extension link relative to said extension portion of said second lower extension link in said brace mechanism.*

*17. The brace mechanism of claim 16 wherein said stop means comprises first and second moveable stops on said fourth link arranged on each side of said second link.*

*18. The brace mechanism of claim 12 comprising further, locking means for locking said brace mechanism with said extension links aligned.*

*19. The brace mechanism of claim 18 wherein said third connecting link includes a tab extension which aligns with said extension portion of said first extension link on alignment of said two extension links, said locking means comprising a slide collar slidable on said extension portion of said first extension link and engageable around said tab extension to lock said tab extension to said first extension link thereby locking said brace mechanism.*

*20. The brace mechanism of claim 14 having further, stop means for limiting the articulation of said brace mechanism in one direction for alignment of said two extension members.*

* * * * *